(12) United States Patent
Lee

(10) Patent No.: US 6,753,159 B1
(45) Date of Patent: Jun. 22, 2004

(54) URIC ACID ASSAY DEVICE WITH STABILIZED URICASE REAGENT COMPOSITION

(76) Inventor: Jin Po Lee, 13150 Glen Cir., Poway, CA (US) 92064

( * ) Notice: Subject to any disclaimer, the term of this patent is extended or adjusted under 35 U.S.C. 154(b) by 0 days.

(21) Appl. No.: 10/130,320

(22) PCT Filed: Aug. 6, 1998

(86) PCT No.: PCT/US98/17483

§ 371 (c)(1),
(2), (4) Date: Nov. 8, 2001

(87) PCT Pub. No.: WO00/08207

PCT Pub. Date: Feb. 17, 2000

(51) Int. Cl.[7] .............................. C12Q 1/58; C12Q 1/62; G01N 33/53
(52) U.S. Cl. ........................ 435/12; 435/10; 435/287.1; 435/970
(58) Field of Search ............................ 435/12, 10, 970, 435/287.1

(56) References Cited

U.S. PATENT DOCUMENTS

| 3,552,925 A | 1/1971 | Fetter ........................... 435/10 |
| 3,649,198 A | 3/1972 | Rush ............................ 435/10 |
| 3,928,137 A | 12/1975 | Monte et al. .................. 435/10 |
| 4,228,240 A | 10/1980 | Dawson et al. ............. 435/188 |
| 4,291,121 A * | 9/1981 | Acquati et al. ................ 435/10 |
| 4,427,770 A | 1/1984 | Chen et al. ................... 435/14 |
| 4,826,761 A | 5/1989 | Arai et al. .................... 435/11 |
| 5,116,729 A | 5/1992 | Ismail et al. .................. 435/14 |
| 5,238,818 A | 8/1993 | Hashizume et al. .......... 435/28 |
| 5,384,248 A * | 1/1995 | Sakata et al. ................. 435/25 |

* cited by examiner

*Primary Examiner*—Louise N. Leary
(74) *Attorney, Agent, or Firm*—Stacy L. Taylor; Foley & Lardner

(57) ABSTRACT

The invention provides an enzyme-based device and process for manufacture of the device in a shelf-stable form. The device consists of a dry phase test strip useful in detecting the presence and concentration of uric acid in a liquid sample (such as urine) and has a stabilized uricase-containing working solution impregnated therein. Methods for manufacturing the device to maintain the stability of the working solution, especially the enzyme components therof, are also described. A method for making the uric acid measurement in one step is also provided, wherein the one step to be performed consists of applying the liquid sample to the test strip of the device.

32 Claims, No Drawings

URIC ACID ASSAY DEVICE WITH STABILIZED URICASE REAGENT COMPOSITION

BACKGROUND OF THE INVENTION

1. Field of the Invention

The invention is an assay device useful in determining the presence and concentration of uric acid in a liquid sample, such as urine.

2. History of the Invention

Dry phase analyte assay test strips (also known as "one-step" assays, requiring only addition of sample to the test strip) to detect the presence or concentration of analytes such as glucose and hormones in body fluids are widely used in clinical laboratories, physician's offices, hospitals, and homes. Important advantages of such test strips include low cost, ease of use, relatively accurate assays and a short response time. However, the manufacture of test strips for one-step is detection of uric acid has been hampered by thermal instability of the uricase enzyme reagent, whose activity can be quickly impaired under common conditions of manufacturing, storage and use (especially with fluids samples of variable pH, such as urine). Thus, uric acid is typically measured in blood or serum using multiple step liquid sample assay protocols.

SUMMARY OF THE INVENTION

The invention consists of a one-step test strip and methods for its use in detecting the presence and concentration of uric acid in liquid samples, including urine. The test strips include a patch impregnated with a working solution, including stabilized uricase. The test strips of the invention are stable in that they can be stored for relatively long periods of time without loss of uricase activity.

In particular, the test strips consist of a porous material impregnated with an enzyme-stabilized, pH-controlled, buffered working solution in which uricase is stabilized against thermal degradation The unicase reagent is further protected against degradation during manufacture of the test strips by use of a process consisting of impregnation of the strip with the working solution and drying to remove solvent. Application of the working solution may be followed by a second impregnation of the test strip with a concentrated buffer. Thus, if the buffer in the working solution has a salt concentration (using phosphate salt as an example) of about 1M and a pH of 8.5 to 9.5, no second application of buffer is required. However, if a working solution having a buffer with a salt concentration of 50 mM to 2M and a pH between 6.5 and 7.0 is utilized, impregnation of the working solution is followed by drying of the test strip and application of more concentrated buffer with a similar pH.

For use in detection of uric acid, a visually detectable signal indicative of the presence and/or concentration of uric acid present in an analyte sample is incorporated into the test strip. Conveniently, the visually detectable signal is produced by a color-forming entity, such as a chromogen.

Kits incorporating the test strips of the invention are also provided. Components of the kits may include test strips, color charts for comparison to color observed after assay performance using the test strips and storage containers for the test strips after use in an assay (for subsequent reference).

Other features and advantages of the invention, eg., stable test strips useful for determining uric acid levels, will be apparent from the following detailed description, the drawings, the Examples and from the claims.

DETAILED DESCRIPTION OF THE INVENTION

Unless other defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present application, including definitions, will control. In addition, the materials, methods, and examples described herein are illustrative only and not intended to be limiting.

Uricase Reagent Composition and Process for Manufacture of Uric Acid Test Strips

Composition

The uric acid detection device of the invention consists of a dry phase test strip impregnated with a stabilized working solution for the semi-quantitative detection of uric acid in a liquid sample. The assay is reliable, accurate and trustworthy because the enzyme reagent composition sufficiently maintains its enzymatic and chemical activity over time, provided the instructions on the container to keep the test strips dry are followed (e.g., storage in an air-tight container including a dessicant).

More specifically, the test strips consist of porous material bound to a non-porous substrate. The stabilized working solution is impregnated into an exposed surface of the porous material.

The working solution is an aqueous solution containing a buffer. To limit the number of applications of working solution to the test strip required, the buffer in the working solution is one which buffers in the pH range of about 8.5–9.5, preferably about 8.8–9.2 and most preferably at a pH of about 9.0. The buffer can generally be any buffer that buffers in these ranges, such as a citrate or phosphate buffer (desirably the latter). The phosphate buffer may consist of salts such as salts of potassium, sodium and the like and will have a concentration of salt of at least about 1M.

Alternatively, a working solution having a buffer of a lower pH (6.5 to 7.5, preferably 7.0) and a salt concentration in a range of 50 mM to 2M (preferably 50 mM) may be applied to the test strip, which is then dried. Drying is followed by application of a buffer to the test strip which has a pH within the range of 6.5 to 7.5 (preferably 7.0 pH) and a higher concentration of salt (preferably 200 mM) than is present in the working solution. After the application of concentrated buffer solution, the test strip is again dried.

Also included in the working solution is a chromogen which produces a color change on the test strip indicative of the presence of uric acid in the sample. Although many chromogens are known in the art, the most convenient uses the catalytic reaction between uricase and any uric acid present in the analyte sample to produce a color change on the test strip whose appearance and intensity permits both detection of uric acid in the sample and estimation of its concentration.

In human urine the first pKa of uric acid is 5.57. At or above a pH of 5.57, uric acid exists mainly as the urate ion which is more soluble than uric acid. At a pH below 5.57, uric acid is the predominant form. The enzyme uricase converts urate ions and uric acid to allantoin and hydrogen peroxide. In the presence of an oxidizable chromogen system, this uricase-uric acid reaction produces color. Thus, the working solution includes both uricase (conveniently of a bacterial source) and an oxidizable chromogen composition.

An example of an oxidizable chromogen composition suitable for use in the invention is produced by combining a color-forming coupler such as 3,5-dichloro-2-hydroxybenzenesulfonic acid (DHBS) with an oxidizable color developing compound such as 4-aminophenazone to form a chromogen composition which, in the presence of peroxidase, produces a color indicative of the presence of analyte in a sample. The peroxidase reaction using this chromogen composition results in differing concentrations of the colored product N-(4-antipyryl)-3-chloro-5-sulfonate-p-benzoquinone-monoimine depending on the concentration of uric acid in the liquid sample. Hence different colors and intensity of color are obtained at differing urine uric acid levels. Those of ordinary skill in the art will be familiar with other chromogen compositions which may be used in the invention; for example, those described in U.S. Pat. No. 4,672,029 (peroxidase reactive chromogen compositions comprised of heterocyclic compounds mixed with oxidizable color developing compounds).

Another component of the working solution is an agent that neutralizes ascorbic acid (frequently found in urine) to prevent its interference with reaction between the uricase in the reagent composition and any uric acid in the sample. Appropriate ascorbic acid neutralizers are known in the art and include heavy metal compounds containing cobalt, iron, mercury, or nickel, $Co(NH_3)_6Cl_3$, the ferric chelate of N-(hydroxyethyl)-ethylenediaminetriacetic acid, bromate ions, chlorate ions, perchlorate ions, chromate ions, organic peroxides, organic hydroperoxides, organic N-halo compounds or ascorbate oxidase. Ascorbate oxidase oxidizes ascorbic acid to its inert form, dehydroascorbic acid and is a convenient ascorbic acid neutralizer for use in the invention.

An enzyme stabilizer may also be a component of the working solution. One example of an enzyme stabilizer is a surfactant. Particularly advantageous surfactants for use in the invention include those described in U.S. Pat. No. 3,928,137 (polyoxyalkylene nonionic surfactants having polyoxypropylene chains with a molecular weight between 750 and 6750, constituting 10–80% of the weight of the surfactant), although commonly available surfactants such as Triton X-100, Tween-20, sodium lauryl sarcosinate or polyethylene glycol will also suffice. In the working solution, the surfactant serves to both stabilize the enzymes and allow for more uniform coating of the absorbent material with the enzyme reagent composition and hence greater uniformity of color development and improved color differentiation in the test strip before and after contacting with test sample.

A desirable alternative to a surfadant for use in stabilizing the enzyme component of the working solution is a polysaccharide or sugar, such as sucrose (e.g., 0.05% to 10% w/v sucrose), lactose, glucose or the like. The sugar stabilizes both the uricase and peroxidase enzymes used during preparation of the assay device.

Bilirubin is frequently found in urine and has the potential to exert negative chemical interference with the peroxidase systems. This problem is obviated in the test strip of the invention by utilizing potassium ferrocyanide as the oxygen acceptor and the DHBS/4-aminophenazone pair as the chromogenic composition. Ferricyanide (produced by oxidation of ferrocyanide in the presence of peroxidase) oxidizes the chromogenic composition. This reaction involves a phenol intermediate that does not react with bilirubin.

Each of the components of the working solution are mixed in a solvent, preferably a neutral, non-organic solvent such as water or normal saline. Table 1 lists the components and their concentrations in a preferred working solution in which the solvent is distilled water. All of the components of the working solution identified in the Table are commercially available from sources which will be known to, or can be readily ascertained by, those of ordinary skill in the art.

TABLE 1

WORKING SOLUTION

| COMPONENT | CONCENTRATION |
| --- | --- |
| Phosphate Buffer | 50 mM to 2.0M or more, pH 6.5 to 7.5 (double impregnation); or 1.0M to 2.0M, pH 8.5 to 9.5 (single impregnation) |
| Horseradish peroxidase | 0.15 kU/L to 1000 kU/L |
| Ascorbate oxidase | 0.15 kU/L to 5 kU/L |
| 4-aminophenazone | 0.25 mM to 50 mM |
| Potassium ferrocyanide | 30 uM to 20 mM |
| DHBS | 2 mM to 200 mM |
| Sucrose | 0.05% to 10% w/v |
| Uricase | 0.05 kU/L to 25,000 kU/L |

Kits for Use of the Test Strips

For convenience, the test strips of the invention may be provided to the end user as part of a kit. Components of the kits may include test strips, color charts appropriate to the liquid to be assayed for comparison to color observed after assay is performance using the test strips, specimen containers, labels and storage containers for the test strips after use in an assay procedure (for subsequent reference).

Process for Manufacture of Test Strips

The absorbent material which is impregnated with the working solution can be any substance capable of incorporating the components of the enzyme reagent composition. The material must be substantially inert with respect to the enzyme reagent composition and must be porous and/or absorbent relative to the liquid sample to be tested, e.g., urine. The substance can be either bibulous matrices or nonbibulous matrices that are insoluble in, and maintain their structural integrity when exposed to, aqueous solutions or physiological fluids. Bibulous matrices that can be useful for the devices of the present invention include but are not limited to, paper, sponge materials, cellulose, hydrophilic inorganic powders, wood, synthetic resin fleeces, woven and nonwoven fabrics and like materials. Nonlimiting examples of nonbibulous matrices include glass fiber, permeable polymer films and preformed or microporous membranes.

The enzyme reagent composition is incorporated into the paper by any method such as dipping, spreading or spraying. A preferred method of incorporation involves dipping the paper into the working solution then drying to remove the solvent. Drying can be by any method that does not deleteriously affect the reagents incorporated into the absorbent material. The usual drying method is by means of an air oven at 37 to 60° C.

After drying, the absorbent material may be impregnated with a second buffer solution with a pH of about 6.5–7.5, preferably about 7.0, in which the salt of the buffer is more concentrated than the buffer of the working solution. In a particularly useful example, where the buffer of the working solution has a salt concentration of 50 mM, the salt concentration of the buffer used in the second impregnation will be 4 times as concentrated; i.e., 200 mM. The second impregnation with the concentrated buffer effectively maintains an optimum pH in the device of the invention.

Alternatively, the pH optimum can be maintained in the device by use of a single working solution treatment, wherein the phosphate buffer has a concentration of at least about 1M (up to 2M) and the pH of the buffer is increased to within the range of 8.5 to 9.5, preferably about 9.0.

After the second impregnation (or single impregnation if the higher pH buffer is applied) the absorbent material is dried again and affixed, via a double-sided adhesive (e.g., two sided adhesive tape), to a solid moisture impervious support. This support can be constructed from, for example, hydrophobic plastic, cellulose acetate, polyethylene, terephthalate, polycarbonate, or polystyrene.

Conveniently, the test strip will consist of a single, working solution-impregnated porous membrane affixed to a solid support having a handle, plastic strip or other means to enable the strip to be handled by the user without contacting the porous membrane. However, those of ordinary skill in the art will recognize that the test strips may be constructed in many forms; e.g., as a "dipstick" for immersion into a liquid sample, as an open strip onto which sample is applied dropwise or as an enclosed strip placed inside a cassette housing having ports through which any color change occurring on the sMtp after addition of analyte may be observed. The test strip may be formed of one or more layers of porous material placed in fluid communication with one another. For example, a first porous strip may be utilized as a sample receiving zone for immersion in, or receiving dropwise, a liquid analyte sample. The sample receiving zone may be placed on the non-porous substrate in fluid communication with a second porous membrane, wherein the latter includes one or more reagent zones, at least one of which will include the working solution of the invention. The topmost porous membrane may be coated with gelatin to enhance the life of the strip and clarity of any visible reactions produced in the assay.

Numerous other design variations of dipstick, open strip or cassette test strip devices for use in analyte assays are well known in the art and can be readily constructed by those of ordinary skill in the art. Examples of such device design variants which may be adapted for use in the invention can be found in U.S. Pat. Nos. 5,622,871 and 5,602,040, as well as in commonly assigned U.S. Pat. No. 5,384,264.

Method for Measuring Uric Acid

The method of the invention provides a one-step convenient assay for uric acid in a test liquid sample and involves dipping the test strip into the test sample for a time sufficient to saturate the test patch with the sample. The test sample can be a biological fluid such as urine, serum, plasma or sweat or a non-biological fluid such as water from some ecological niche, e.g., a river or a lake, or a solution used in a laboratory. The test sample is preferably fresh uncentrifuged urine from a mammal, e.g., a human, a non-human primate, a dog, a cat, a cow, a horse, a pig, a sheep, a rabbit, a guinea pig, or a rodent such as a mouse, a rat, or a hamster.

After waiting a predetetermined time, such as 60 seconds to about 5 minutes, the test strip is examined, either visually or by an instrument, for a response. The color transition, if any, of the test patch reveals the presence or concentration of uric acid in the urine sample. In many cases, simple visual observation of the test strip provides the desired information, e.g., the presence or absence of uric acids. If more is accurate measurements are required, a color chart bearing color spots corresponding to known concentrations of uric acid can be prepared for the particular enzyme reagent composition used on the test strip. The resulting color of the test strip after contact with the test sample can then be compared with the color spots on the chart to determine the concentration of uric acid in the test sample.

For example, at uric acid levels of 0 mg/dL, 35 mg/dL, 70 mg/dL and 100 mg/dL the colors produced on the test strip of the invention whose uricase reagent components are described in Table 1 and respectively, light cream, light pink, magenta and dark magenta.

In addition, the test strip can be made quantitative by employing spectrophotometric or colorimetric techniques, as opposed to visual techniques, in order to more reliably and more accurately measure the degree of color transition, and therefore more accurately measure the concentration of uric acid in the liquid test sample, especially at low concentrations such as below 1 mg uric acid/dL of liquid sample.

The following examples are meant to illustrate the invention and not to limit it. All abbreviations used in the Examples have their commonly accepted meaning (e.g., "ml" for milliliters) unless otherwise indicated.

EXAMPLE I

Perpetration of an Uric Acid Assay Device

A. Preparation of Working Solution 1L of a working reagent solution at pH 9.0 were prepared with the following components in $dH_2O$:

| | |
|---|---|
| a. Potassium Phosphate, Dibasic Anhydrous | 1M |
| b. 4-Aminophenazone | 30 mM |
| c. DHBS | 60 mM |
| d. KFeCN | 4 mM |
| e. Uricase enzyme (*Candida utilis*) | 5 KU/ml |
| f. Horseradish Peroxidase | 1K U/ml |
| g. Ascorbate Oxidase | 200 U/ml |
| h. Sucrose | 10.0% w/v |

B. Preparation of Urinalysis Dipstick

Absorbent paper #593 (Lot # N952) from Schleicher & Schuell were dipped into the above working reagent solution until saturated. The coated paper were then dried in an incubator at 40° C. Double sided adhesive tape from 3M was then applied to one side of the coated dried paper. The paper was then affixed to an inert plastic strip and cut into 5 $mm^2$. The squares were stored in an air tight plastic container with desiccant ready for use.

C. Preparation of Standards

Uric acid purchased from Sigma were dissolved in uric acid negative urine base pH 6.5 and value assigned using a marketed liquid reagent Uric Acid Assay (purchased from Teco). The levels assigned to the standards were: 0, 35, 85, 140 mg/dl. The standards were assayed using the above prepared test strips and a picture color chart representing each level was developed and used as reference.

D. Patient Correlation 247 adult samples from an apparently healthy normal population at Carlsbad, Calif. were assayed using the above prepared test strips and the Teco Liquid Reagent Uric Assay. The upper limit of normal (15%) for the tested population was 78 mg/dl. The resulting concordant data are as follows:

CONCORDANCE TABLE

| Test Strips | TECO POSITIVE | TECO NEGATIVE |
| --- | --- | --- |
| POSITIVE | 31 | 0 |
| NEGATIVE | 6 | 210 |

| | |
| --- | --- |
| Relative Sensitivity = | 83.78% |
| Relative Specificity = | 100.00% |
| Relative Accuracy = | 97.57% |

EXAMPLE II
Device Resistance to Sample Component Interference
A. Affect of Sample pH on Uric Acid Test Strips Uric acid standards were prepared as Example I above at the following pH: 4.5, 5.5, 6.5, 7.5 and 8.5. The standards were then assayed using the test strips prepared from Example I. Corresponding standards from different pH levels produced the same visual result demonstrating that the pH of the patient samples does not affect or interfere with the assay.

B. Affect of Ascorbic Acid on Uric Acid Test Strips

Uric acid standards were prepared as Example I above at a pH of 6.5 and spiked with the following levels of ascorbic acid: 25, 50, 75 and 100 mg/dl. The spiked standards were then assayed using the test strips prepared from Example I above and compared against the color reference chart. No ascorbic acid interference was observed for any of the standards.

C. Bilirubin Interference of Uric Acid Test Strips

Uric acid standards were prepared as Example I above at a pH of 6.5 and spiked with the following levels of Bilirubin: 10, 20, 30 and 40 mg/dl. The spiked standards were then assayed using the test strips prepared from Example I above and compared against the color reference chart. No Bilirubin interference was observed for any of the standards.

Although the invention has been described with reference to the presently preferred embodiment, it should be understood that various modifications can be made without departing from the spirit of the invention. All such modifications are within the scope of the invention, which is defined by the following claims.

What is claimed is:

1. An assay device for determination of the presence and concentration of uric acid in a liquid sample comprising:
   a reagent test patch; and,
   a working solution applied to the reagent test patch, the working solution comprising an enzyme stabilizer, uricase, a chromogen system, an oxygen acceptor and a buffer that buffers the solution to a pH of 8.5 to 9.5 and has a salt concentration of 1.0 to 2.0M;
wherein the reagent test patch is dried after application of the working solution.

2. The device of claim 1, wherein the liquid sample is a urine sample from a mammal.

3. The device of claim 1, wherein the chromogen system comprises a coupling pair consisting of 3,5-dichloro-2-hydroxybenzenesulfonic acid and 4-aminophenazone and a reactant consisting of peroxidase.

4. The device of claim 1, wherein the buffer buffers to a pH of 9.0.

5. The device of claim 4, wherein the buffer has a salt concentration of 1M.

6. The device of claim 1, wherein the enzyme stabilizer comprises a sugar.

7. The device of claim 6, wherein the sugar is selected from the group of sugars consisting of sucrose, lactose and glucose.

8. The device according to claim 7, wherein the sugar is sucrose added to the working solution at a concentration of 0.05% to 1.0% w v.

9. The device of claim 1, wherein the buffer is phosphate buffer.

10. The device of claim 1, further comprising ascorbate oxidase.

11. The device of claim 1, wherein the oxygen acceptor is potassium ferrocyanide.

12. An assay device for determination of the presence and concentration of uric acid in a liquid sample comprising:
    a reagent test patch; and,
    a working solution applied to the reagent test patch, the working solution comprising an enzyme stabilizer, uricase, a chromogen system, an oxygen acceptor and a first buffer that buffers the solution to a pH of 6.5 to 7.5 and has a salt concentration of 50 mM to 2.0M;
wherein the reagent test patch is dried after application of the first working solution, then a second buffer having a pH of 6.5 to 7.5 and a salt concentration greater than the salt concentration of the first buffer is applied to the reagent test patch, which is then dried.

13. The device of claim 12, wherein the liquid sample is a urine sample from a mammal.

14. The device of claim 12, wherein the chromogen system comprises a coupling pair consisting of 3,5-dichloro-2-hydroxybenzenesulfonic acid and 4-aminophenazone and a reactant consisting of peroxidase.

15. The device of claim 12, wherein the first buffer buffers to a pH of 7.0.

16. The device of claim 12, wherein the first buffer has a salt concentration of 50 mM.

17. The device of claim 12, wherein the second buffer buffers to a pH of 7.0.

18. The device of claim 17, wherein the second buffer has a salt concentration of 200 mM.

19. The device of claim 12, wherein the enzyme stabilizer comprises a sugar.

20. The device of claim 19, wherein the sugar is selected from the group of sugars consisting of sucrose, lactose and glucose.

21. The device of claim 20, wherein the sugar is sucrose added to the working solution at a concentration of 0.05% to 1.0% w/v.

22. The device of claim 12, wherein each buffer is a phosphate buffer.

23. The device of claim 12, further comprising ascorbate oxidase.

24. The device of claim 12, wherein the oxygen acceptor is potassium ferrocyanide.

25. An assay device for determination of the presence and concentration of uric acid in a liquid sample comprising:
    a reagent test patch; and,
    a stabilized working solution applied to the reagent test patch, the working solution comprising a sugar, uricase, a chromogen system, an oxygen acceptor and a buffer that buffers the solution to a pH of 8.5 to 9.5 and has a salt concentration of 1.0 to 2.0M;
wherein the reagent test patch is dried after application of the working solution.

26. The device of claim 25, wherein the sugar is selected from the group of sugars consisting of sucrose, lactose and glucose.

27. The device of claim 26, wherein the sugar is sucrose added to the working solution at a concentration of 0.05% to 1.0% w/v.

28. An assay device for determination of the presence and concentration of uric acid in a liquid sample comprising:
   a reagent test patch; and,
   a working solution applied to the reagent test patch, the working solution comprising uricase, sugar, a chromogen system, an oxygen acceptor and a first buffer that buffers the solution to a pH of 6.5 to 7.5 and has a salt concentration of 50 mM to 2.0M;
wherein the reagent test patch is dried after application of the first working solution, then a second buffer having a pH of 6.5 to 7.5 and a salt concentration greater than the salt concentration of the first buffer is applied to the reagent test patch, which is then dried.

29. The device of claim 28, wherein the sugar is selected firm the group of sugars consisting of sucrose, lactose and glucose.

30. The device of claim 29, wherein the sugar is sucrose added to the working solution at a concentration of 0.05% to 1.0% w/v.

31. A method of determining whether uric acid in a liquid sample using the detection device of claim 1, claim 10, claim 25 or claim 28, the method comprising:

(a) contacting the reagent test patch with the liquid sample; and
   (b) observing whether a change in color occurs on the reagent test patch,
   wherein a change in color indicates that uric acid is present in the liquid sample.

32. The method of claim 31, wherein the liquid sample is a urine sample from a mammal.

* * * * *